(12) United States Patent
Bertocci et al.

(10) Patent No.: US 12,558,072 B2
(45) Date of Patent: Feb. 24, 2026

(54) ULTRASOUND PROBE WITH IMPROVED THERMAL MANAGEMENT

(71) Applicant: ESAOTE S.p.A, Genoa (IT)

(72) Inventors: Francesco Bertocci, Santa Maria a Monte (IT); Michele Bassani, Florence (IT); Ramona De Luca, Florence (IT)

(73) Assignee: ESAOTE S.p.A, Genoa (IT)

( * ) Notice: Subject to any disclaimer, the term of this patent is extended or adjusted under 35 U.S.C. 154(b) by 862 days.

(21) Appl. No.: 17/073,159

(22) Filed: Oct. 16, 2020

(65) Prior Publication Data

US 2021/0121159 A1       Apr. 29, 2021

(30) Foreign Application Priority Data

Oct. 23, 2019     (EP) .................................... 19204937

(51) Int. Cl.
   *A61B 8/00*          (2006.01)
   *G01S 15/89*         (2006.01)
(52) U.S. Cl.
   CPC ............ *A61B 8/546* (2013.01); *A61B 8/4494* (2013.01); *G01S 15/899* (2013.01)
(58) Field of Classification Search
   CPC ..... A61B 8/546; A61B 8/4494; A61B 8/4483; G01S 15/899; B06B 1/0622; B06B 1/0677
   See application file for complete search history.

(56) References Cited

U.S. PATENT DOCUMENTS

| | | |
|---|---|---|
| 4,825,115 A | 4/1989 | Kawabe et al. |
| 5,267,221 A | 11/1993 | Miller et al. |
| 5,329,498 A | 7/1994 | Greenstein |
| 5,545,942 A | 8/1996 | Jaster et al. |
| 5,560,362 A | 10/1996 | Sliwa, Jr. et al. |
| 5,721,463 A | 2/1998 | Snyder |
| 5,961,465 A | 10/1999 | Kelly, Jr. et al. |
| 7,052,463 B2 | 5/2006 | Peszynski et al. |
| 7,105,986 B2 | 9/2006 | Wildes et al. |
| 7,308,828 B2 | 12/2007 | Hashimoto |
| 7,621,028 B2 | 11/2009 | Gelly et al. |

(Continued)

FOREIGN PATENT DOCUMENTS

| | | | |
|---|---|---|---|
| CN | 110960252 A | * | 4/2020 |
| EP | 2992829 A1 | | 3/2016 |
| WO | 2012156886 A1 | | 11/2012 |

OTHER PUBLICATIONS

Extended European Search Report dated Apr. 3, 2020, which issued in corresponding EP Patent Application No. 19204937.7.

*Primary Examiner* — Pascal M Bui Pho
*Assistant Examiner* — Michael Yiming Fang
(74) *Attorney, Agent, or Firm* — Dickinson Wright PLLC

(57)                ABSTRACT

A transducer assembly operable to transmit ultrasonic energy in a desired direction towards a zone adapted to be acoustically coupled to an object or area of interest is provided that has: a transducer layer; a backing layer disposed behind said transducer layer with respect to the desired direction; a back-matching layer disposed between the transducer layer and the backing layer to reflect towards said transducer layer part of the ultrasonic energy directed from the transducer layer to the backing layer; and a heat transfer layer disposed between the back-matching layer and the backing layer to drain heat from the transducer assembly. A process for manufacturing a transducer assembly is also disclosed.

14 Claims, 15 Drawing Sheets

(56) References Cited

U.S. PATENT DOCUMENTS

| | | | | |
|---|---|---|---|---|
| 7,694,406 | B2 | 4/2010 | Wildes et al. | |
| 2010/0327698 | A1* | 12/2010 | Guo ..................... | G10K 11/002 |
| | | | | 310/335 |
| 2013/0085396 | A1* | 4/2013 | Isono ................... | A61B 8/4455 |
| | | | | 600/472 |
| 2014/0062261 | A1* | 3/2014 | Yamamoto ........... | H01L 41/338 |
| | | | | 310/334 |
| 2014/0375171 | A1* | 12/2014 | Tai ........................ | B06B 1/0622 |
| | | | | 310/341 |
| 2015/0327839 | A1* | 11/2015 | Kim ........................ | A61B 8/14 |
| | | | | 600/447 |
| 2017/0043189 | A1* | 2/2017 | Stoddard .................. | A61N 7/02 |
| 2018/0290175 | A1 | 10/2018 | Palchetti et al. | |
| 2020/0196992 | A1* | 6/2020 | Li .......................... | B06B 1/067 |

* cited by examiner

P → Piezoelectric material

1 → Acoustic mirror

B → Backing

P → Piezoelectric material

1 → Acoustic mirror

2 → Thermal layer

B → Backing

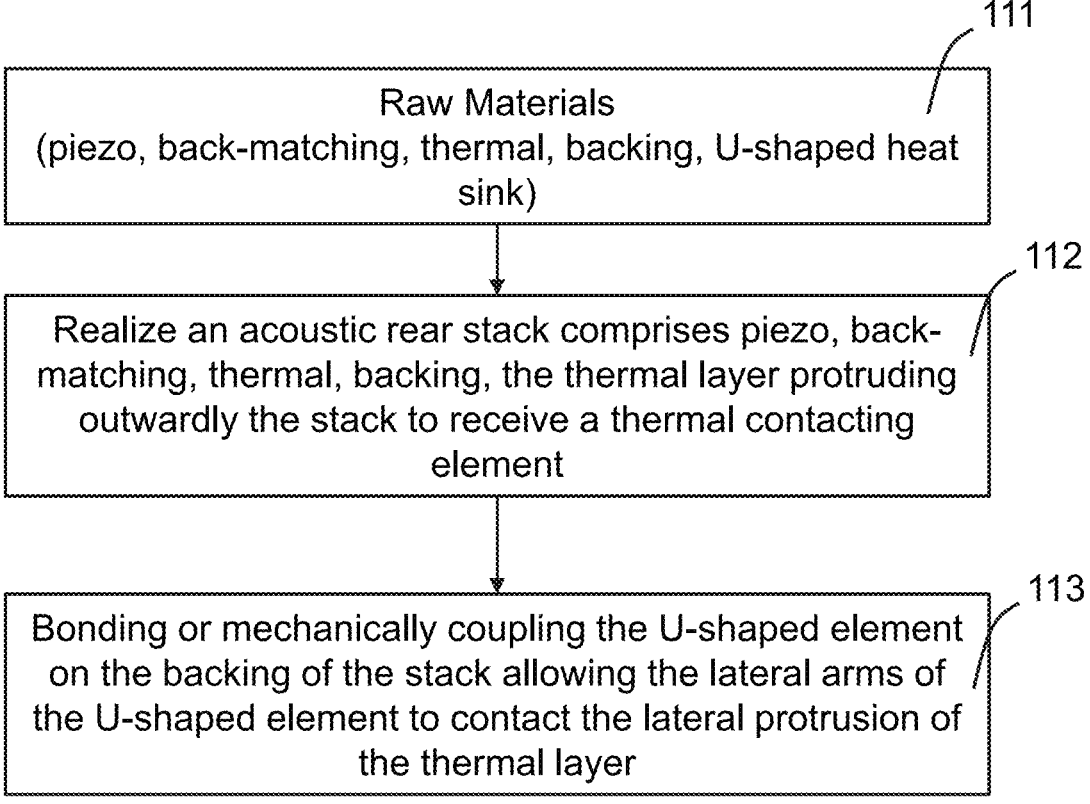

111

Raw Materials
(piezo, back-matching, thermal, backing, U-shaped heat sink)

112

Realize an acoustic rear stack comprises piezo, back-matching, thermal, backing, the thermal layer protruding outwardly the stack to receive a thermal contacting element

113

Bonding or mechanically coupling the U-shaped element on the backing of the stack allowing the lateral arms of the U-shaped element to contact the lateral protrusion of the thermal layer

Fig. 20

ULTRASOUND PROBE WITH IMPROVED THERMAL MANAGEMENT

FIELD OF THE INVENTION

The invention relates to the technical field of ultrasound probes, particularly in the medical field, although it can find applications also in the non-destructive testing field.

STATE OF THE ART

Ultrasound diagnostic technology generally relates to imaging of biological tissue using an ultrasonic transducer probe. The probe includes a transducer which transmits ultrasonic waves and receives ultrasonic echoes reflected from the tissue. The transducer is typically placed on the body surface or internal to a body lumen of a patient in a selected imaging region. The ultrasound transducer generates and directs ultrasonic waves to the imaging region. The transducer then receives ultrasonic waves reflected from the region and converts the received waves into electrical signals that are processed to form a diagnostic image.

In the case of ultrasound treatment, high-intensity focused ultrasound energy is applied to locally heat and destroy diseased or damaged tissue. An example is HIFU (High-Intensity Focused Ultrasound), a class of clinical therapies that uses ultrasound-induced hyperthermia to treat diseases. Another application is lithotripsy where acoustic energy is used to destroy stones, typically kidney stones.

In both imaging and therapy applications, an undesirable thermal build-up is created in the probe during transmission due to acoustic losses being converted into heat. Prescribed limits are set or prescribed by governing agencies as to the amount of heat that can be allowed to build up on the surface of the probe, typically limiting the surface temperature of the probe tip to a predetermined temperature or to a predetermined increase above room temperature, and hence limiting the acoustic output. Optimal transducer performance is obtained when the surface temperature of the probe tip is maintained at a specified temperature, such as room temperature, regardless of the acoustic output.

Various methods have been proposed for thermal management in ultrasonic probes. Conventional methods prescribe passive cooling of the transducer structure by transferring heat from the source into the body and handle of the probe.

U.S. Pat. No. 5,545,942 proposes the use of heat conductors to be placed around the periphery of the transducer package, but within the probe housing, so that heat can be drawn away from the transducer face and toward the rear/interior of the probe. The heat conductors act as conduits for draining away heat which builds up in the thermal potting material during pulsation of the piezoelectric transducer elements. The heat conductors are formed from metal foil, typically aluminium, having a heat conductivity greater than the heat conductivity of the thermal potting material which fills the spaces inside the probe housing and surrounds the transducer package.

U.S. Pat. No. 5,721,463 teaches how to use the cable components as heat conductors which conduct heat out of the probe handle. These heat pipes are coupled to an internal heat conductor which is in heat conductive relationship with the transducer pallet. Thus, heat generated by the transducer array can be transferred, via the internal heat conductor plate and the cable heat conductors, away from the probe surface which contacts the patient. Alternatively, inlet and return flow paths for cooling fluid are incorporated in the cable.

The inlet and return flow paths inside the cable are respectively connected to the inlet and outlet of a flow path which is in heat conductive relationship with an internal heat conductor in the probe handle.

In WO 2012156886 the heat developed in the transducer stack is coupled to a metallic frame inside the handle of probe. A metallic heatspreader is thermally coupled to the probe frame to convey heat away from the frame. The heatspreader surrounds the inside of the probe handle and has an outer surface which is thermally coupled to the inner surface of the probe housing. Heat is thereby coupled evenly from the heatspreader into the housing without the development of hotspots in the housing which could be uncomfortable to the hand of the sonographer.

U.S. Pat. Nos. 7,105,986 and 7,694,406 disclose a composite structure of a backing material with enhanced conductivity for use in a transducer. The composite structure includes a plurality of layers of backing material alternatingly arranged with a plurality of thermal conductive elements, wherein the plurality of thermal conductive elements are configured to transfer heat from a center of the transducer to a plurality of points on the composite structure of backing material.

U.S. Pat. No. 5,560,362 teaches active cooling by using an open loop cooling system, a closed loop circulating cooling system, a thermoelectric cooling system and an evaporator/condenser system. U.S. Pat. No. 5,961,465 teaches transferring of heat from integrated circuits located within the housing of the probe and approximating the transducer, where the transfer of heat is provided by a circulating cooling system.

The above methods transfer heat away from, or cool, the portion of the transducer structure that is internal to the probe, and therefore remote from the biological tissue being imaged. However, the primary source of heat generation is the area of the probe closest to the biological tissue, namely, the area of the transducer from which the acoustic energy is transmitted towards the biological tissue, and the adjacent lens in contact with the biological tissue through which the acoustic energy is focused and directed into the biological tissue.

U.S. Pat. No. 7,052,463 discloses an active cooling system which includes a conduit for circulating cooling medium and a heat exchanger in fluid communication with the circulating cooling medium and having means for removing heat from the circulating cooling medium, wherein at least a portion the conduit is in proximity to or contacts the outer surface of the probe tip.

Although efficient, this system requires an active device external to the transducer which renders the probe cumbersome and rather complicated, particularly with reference to passive cooling approach.

A first attempt to drain heat passively from the tip of the probe can be found in the already mentioned U.S. Pat. No. 5,721,463. This document, among various embodiments, teaches a thermal enhancement layer consisting of a film of diamond or diamond-like carbon-based material, which is highly thermally conductive, formed on the acoustic components at the distal end of the probe. This solution goes in the right direction, however, diamond has poor acoustic properties. An acceptable acoustic coupling would thus require an extremely thin film, which limits its ability to work as a heat drain device. Furthermore, a limit exists in the minimal achievable thickness of the layer due to the typical tri-dimensional structure of diamond that renders this solution impracticable.

This limit is smartly overcome in EP Pat. No. 2992829 where a heat transfer device made of a graphene-based material, either pure graphene or a graphene-loaded resin, which is placed on the front of the transducer assembly to act as a matching layer, is disclosed.

A class of efficient probes in terms of thermal properties are those involving a de-matching layer sandwiched between the backing and the piezo-elements.

Back-matching layers are mainly used to reflect the energy transmitted backwards by the piezo-elements and retransmit it forward. This reuse of acoustic energy that would otherwise be dispersed, increases sensitivity and enables less heat dissipation, allowing to achieve higher penetration.

Increase of sensitivity requires a large impedance mismatch between the piezoelectric layer and the back-matching layer to have strong reflection and thus relevant back-propagating energy. This can be achieved both using a material for the back-matching layer having an impedance which is much higher than the impedance of the piezoelectric layer or with a material for the back-matching layer having an impedance which is much lesser than the impedance of the piezoelectric layer.

In document U.S. Pat. No. 7,621,028, the choice of a high acoustic impedance back-matching layer has been adopted to assure high bandwidth, a key parameter of the performance of a transducer. The materials mentioned in this document are typically a Tungsten material; a Tantalum material; a Tungsten Carbide (WC) material; a WC and Cobalt material; a WC, Cobalt and Tantalum Carbide material; a WC, Nickel and Carbide-Molybdenum oxide (Mo2C) material; and a WC, Nickel, Cobalt and Chromium Carbide ($Cr_3C_2$) material all of them having acoustic impedance Z higher than 100 MRayl and high thermal conductivity.

This, although allowing high thermal dissipation, however, poses the following drawbacks:

High Z materials are not easy to cut and bind as they normally contain metals. High impedance brings to tight requirements for piezoelectric and de-matching roughness. Furthermore, infra-element cutting is necessary due to their electrical conductivity;

At frequency higher than 5 MHz the quality of the contact surface bonding between piezo and back-matching layer is critical;

The thickness of the piezo material is λ/4 that represents a problem for high frequency probes.

To overcome these problems, in US application published with n. 2018/0290175 the impedance mismatch is achieved using low Z material such as epoxy, powder/particle filled epoxy, polyurethanes, acrylics or the like.

The acoustic stack proposed in this document, however, although enabling enhanced sensitivity, high signal-to-noise (SNR) ratio and good resolution, has poor thermal efficiency as the material forming the back-matching, as well the backing, has low thermal conductivity.

Thus a need continues to exist to determine an appropriate configuration able to increase the sensitivity of the transducer without significantly affecting the bandwidth, pulse duration and thermal efficiency.

SUMMARY OF THE INVENTION

It is thus an object of embodiments herein to provide an arrangement for limiting the heat build-up near the transducer face, that is simple, effective and, at the same time, does not affect the acoustic properties of the transducer assembly.

In an embodiment, a transducer assembly operable to transmit ultrasonic energy in a desired direction towards a zone adapted to be acoustically coupled to an object or area of interest comprises:

a) a transducer layer;

b) a backing layer disposed behind said transducer layer with respect to the desired direction;

c) a back-matching layer disposed between the transducer layer and the backing layer to reflect towards said transducer layer part of the ultrasonic energy directed from the transducer layer to the backing layer;

d) a heat transfer layer disposed between the back-matching layer and the backing layer to drain heat from the transducer assembly.

The heat transfer layer may advantageously be in thermal communication with a heat dissipating and/or storing device.

In an embodiment, the heat transfer layer is advantageously in contact with the back-matching layer, either directly or through a bonding layer, to optimize heat conduction.

By placing a layer with high acoustic impedance (Z) and high thermal conductivity between the de-matching layer (having typically low acoustic impedance, i.e. less than 10 MRayl, particularly between 2 and 5 MRayl) and the backing (for example hard rubber) and connected to a metal, for example aluminium alloy, heat is conducted from the front surface of the probe into its rear part thus improving thermal efficiency.

In an embodiment, the transducer assembly comprises a heat-conductive element at one side of the assembly contacting the heat transfer layer to drain heat from the assembly. The heat-conducting element may advantageously comprise a lamellar or fin-like heat-conductive structure to dissipate at least partially the drained heat. The heat conducting element is typically in thermal contact with a dissipating or accumulating element.

In a specific configuration, there are two heat-conductive elements at opposite sides of the assembly in thermal contact with the heat transfer layer to drain heat from the assembly.

Such heat-conductive element or elements are preferably in thermal contact with a dissipating or accumulating element located in the rear part of the assembly opposite to the zone adapted to be acoustically coupled to the object or area of interest.

One heat-conductive element may have a slot for receiving a portion of the heat transfer layer or a lateral protrusion thereof to improve mechanical coupling.

In an embodiment, the heat transfer layer extends laterally from the transducer assembly to expose at least one surface suitable for thermal contact, direct and/or indirect through conductive materials, with an element of a thermal circuit.

The thermal circuit may comprise a U-shaped portion, typically a single-piece element having a bracket shape, surrounding the backing layer to form, together with the heat transfer layer, a closed loop circuit around the backing layer.

According to another aspect, the present disclosure relates to a process for manufacturing a transducer assembly operable to transmit ultrasonic energy in a desired direction towards a zone adapted to be acoustically coupled to an object or area of interest, the process comprising:

providing a transducer layer;

providing a backing layer;

providing a back-matching layer;

providing a heat transfer layer:

bonding or casting couples of said transducer layers or subassemblies comprising such transducer layers to obtain a stack having the following order from the zone adapted to be acoustically coupled towards the rear of the probe: transducer layer, back-matching layer, heat transfer layer, backing layer.

Several options are possible for forming the acoustic stack. In an embodiment, the process comprises:

bonding or casting the back-matching layer on the transducer layer to realize a transducer/back-matching subassembly, bonding or casting the heat transfer layer either on the backing layer to realize a heat-transfer/backing subassembly or on the back-matching layer to realize a transducer/back-matching/heat-transfer subassembly;

bonding or casting the heat-transfer/backing subassembly layer with the transducer/back-matching subassembly or the transducer/back-matching/heat-transfer subassembly with the backing layer.

In another embodiment, the process comprises:

bonding or casting the heat transfer layer on the backing layer to realize a heat-transfer/backing subassembly, bonding or casting the back-matching layer on the heat-transfer/backing subassembly to realize a back-matching/heat-transfer/backing subassembly;

bonding or casting the transducer layer on the back-matching/heat-transfer/backing subassembly.

In an advantageous configuration with increased thermal efficiency, the process comprises:

providing a heat-conducting support;

stacking or fixing the backing layer on the heat-conducting support;

thermally connecting the heat-conducting support with the heat transfer layer through heat conductive elements, which heat conductive elements are either single piece with the heat-conducting support to form a U-shaped heat-conducting support or are thermally coupled with the heat-conducting support through thermally conductive material.

The heat conductive elements may have a lamellar structure to at least partially contribute to dissipate heat.

The process, for example with grinding steps, may realize a heat transfer layer which has an axial extension which is greater than the axial extension of the backing layer so that upon stacking the heat transfer layer on the backing layer a peripheral annular band of the heat transfer layer protrudes from the assembly to allow thermal contact with an element of a thermal circuit comprising a heat dissipating and/or storing device.

The heat conductive elements may have apertures for allowing the heat transfer layer or a protrusion thereof to be mechanically coupled. Such apertures may be advantageously realized during the manufacturing process.

Further improvements of the invention will form the subject of the dependent claims.

BRIEF DESCRIPTION OF THE DRAWINGS

The characteristics of the invention and the advantages derived therefrom will be more apparent from the following description of non-limiting embodiments, illustrated in the annexed drawings, in which:

FIG. 17-21 are flowcharts of process for manufacturing a transducer assembly according to embodiments herein.

DETAILED DESCRIPTION OF A PREFERRED EMBODIMENT

Figure 1:
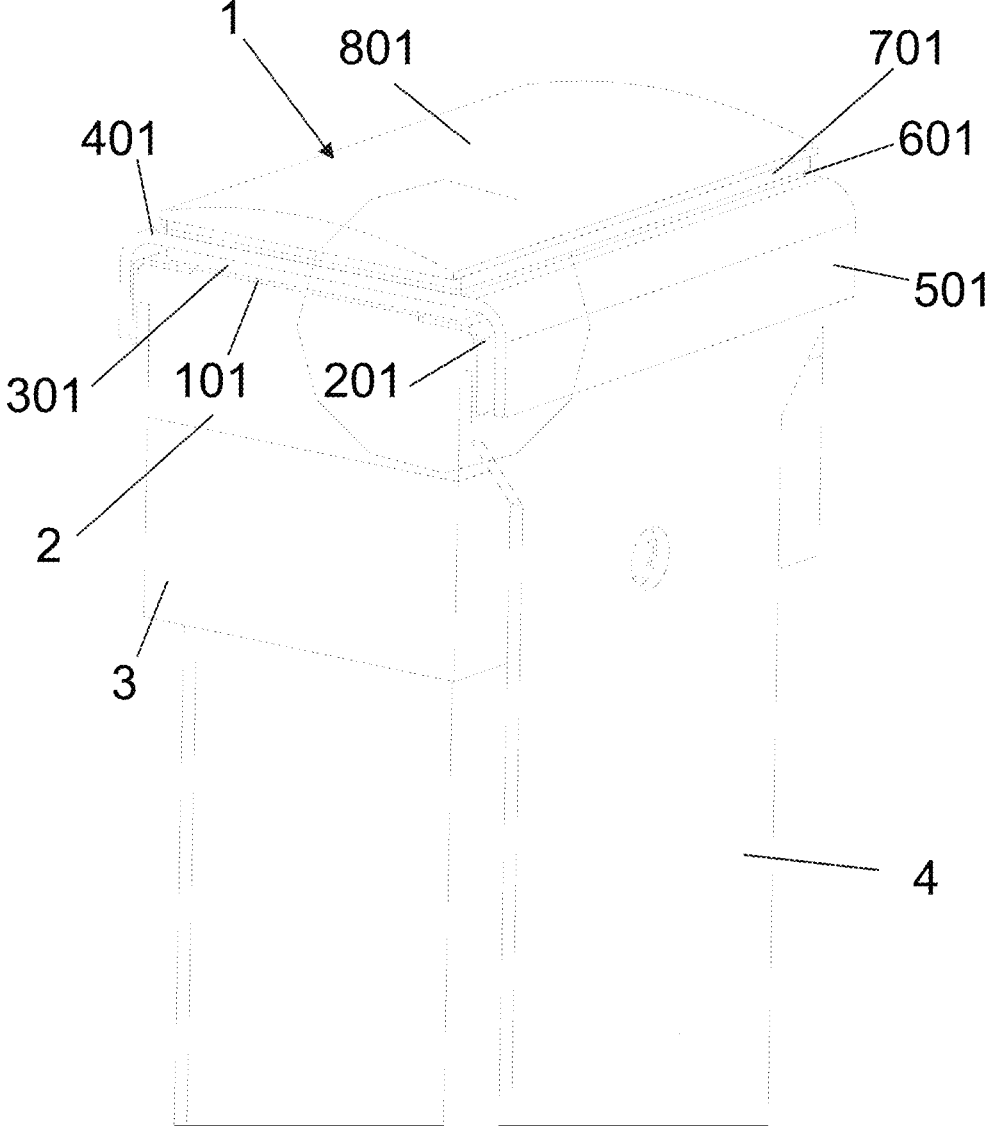
FIG. 1 shows a perspective view of a conventional probe according to the state of the art.
Figure 2:
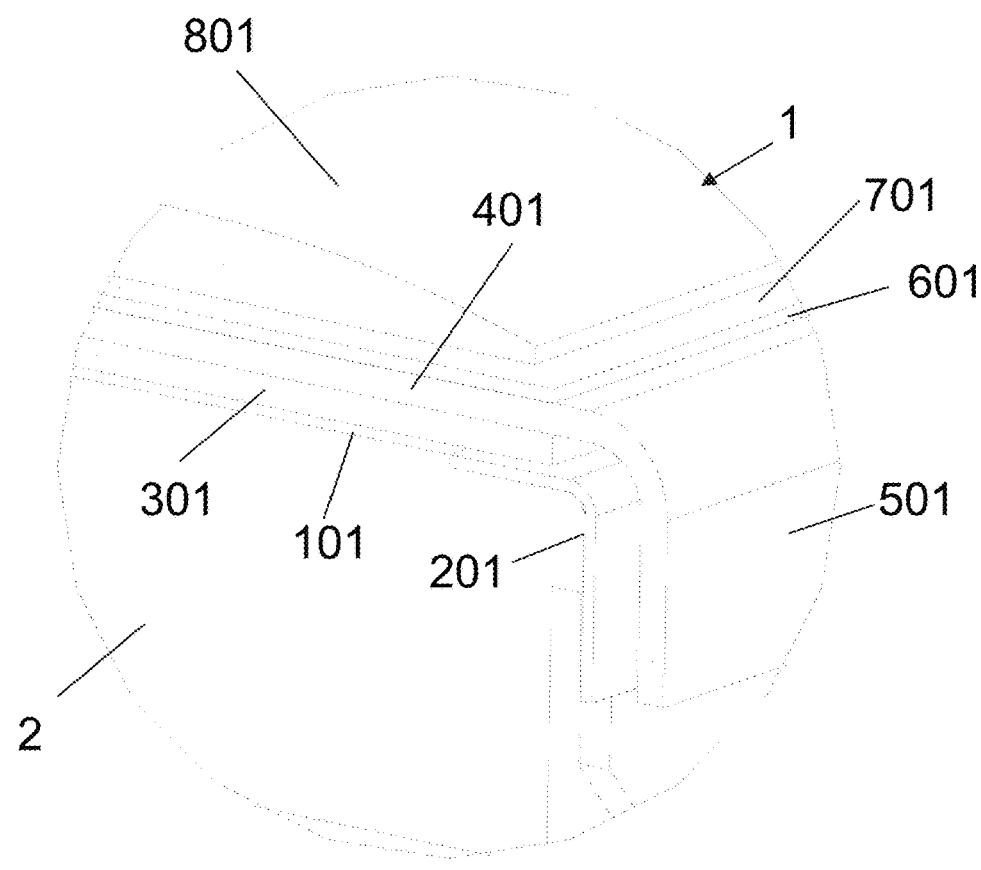
FIG. 2 shows an enlarged view of the head of the probe according to FIG. 1.
Figure 3:
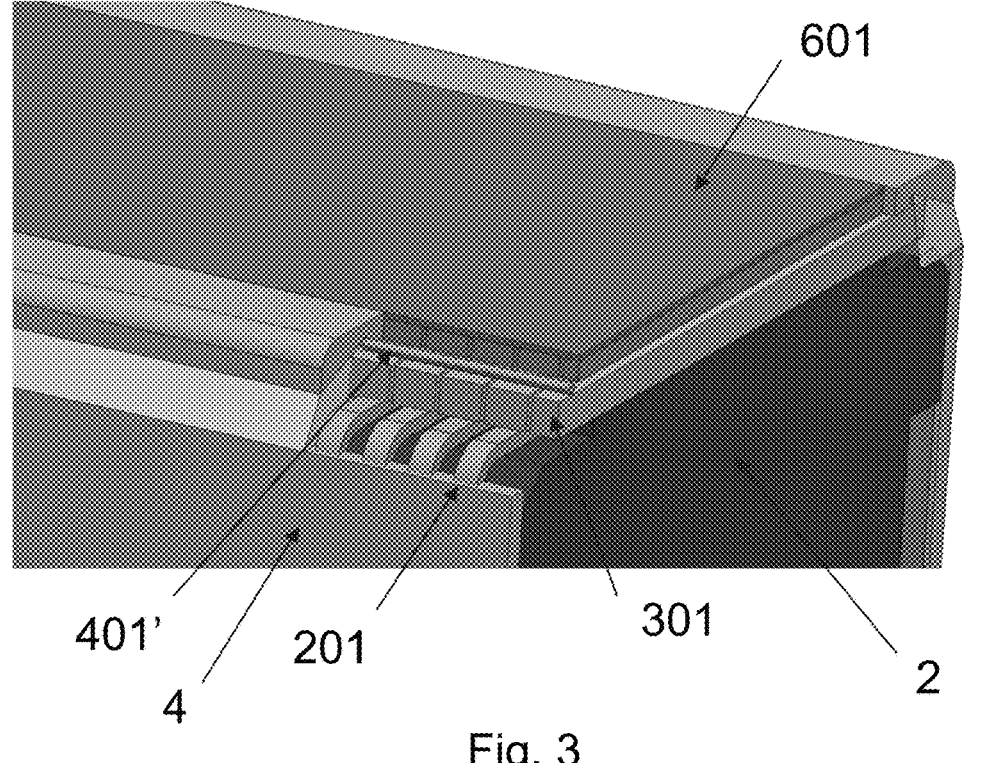
FIG. 3 schematically shows a probe head with ground wire connections arranged to contact transducer elements of a same row.

Referring to FIGS. 1 to 3, a conventional probe is illustrated therein. The probe comprises an ultrasound waves emitting and receiving head 1, which has a front side from which the ultrasound waves are emitted in the direction against a target, such as a body under examination, and on which the reflected ultrasound waves or incoming ultrasound waves impinge and are sensed. The ultrasound head 1 has a back side 3 which is opposite to the said front side and which is oriented towards the inside of a probe casing and towards means for supporting the probe head provided inside the probe casing.

The probe head 1 comprises, in an order starting from the back side of the said head towards the front side of the said head, which order corresponds also to the direction of propagation of the emitted ultrasound waves, a first layer 101 formed by an array of contact electrodes. Each contact electrode of this layer 101 of contact electrodes has a separate electric connection line to a corresponding contact pin on a contact termination provided along at least one edge of the layer of contact electrodes and indicated with 201. The layer 101 of contact electrodes is typically in the form of an array of at least electrically separated contact electrodes since each one of the said contact electrodes has the function of feeding the electric excitation signal to the associated transducer and of collecting the electric receipt signal from the associated transducer when the said transducer is mechanically excited by an impinging ultrasound wave. Some electrodes could be short circuited as in 1.25D, 1.5D or 1.75D probes.

On the layer formed by the array of contact electrodes, an array of piezoelectric elements 301 is laid. Each one of the piezoelectric elements forms an emitting and receiving transducer. Piezoelectric elements are typically fabricated from lead zirconate titanate (PZT), PZT-resin composite or Single Crystal material. The single transducers are each one coincident and in electric contact with one of contact electrodes of the layer 101. In a possible configuration, a further layer of conductive material 401 is laid on the layer 301 formed by the array of transducers. The conductive material of the layer 401 is in electric contact with each one of the said piezoelectric elements and is connected to ground potential by means of a contact termination 501. The layer 401 of conductive material forms the ground electrode of the transducers of the layer 301. The layer 401 may be in the form of an array of ground electrodes, but since the ground potential is common to every of the transducers of the layer 301 there is no need to provide separate ground electrodes for each transducer, so that the said layer 401 can be easily formed by a continuous layer of conductive material. Alternatively, the ground connections may be formed by a microscopic section wire 401' contacting elements belonging to a same raw as shown in FIG. 3. Other ground connection geometries are obviously possible, such as, for example, of the so-called wrap-around type.

On the array of piezoelectric material elements 301 matching layers are provided which are indicated with numerals 601 and 701 in FIGS. 1 and 2. These layers (two in the example of FIG. 2, one in FIG. 3) have the function of adapting the acoustic impedance of the piezoelectric elements to the acoustic impedance of the target. Normally two or three layers are used in order to provide a progressive stepwise adaptation, which also allows to maintain a sufficiently large bandwidth for the passing ultrasound waves. In each material, the acoustic impedance is given by the product of density times speed of sound and can be considered equivalent to the electrical impedance for an electrical circuit with many power transfer stages. The thickness of each matching layer generally follows the $\lambda/4$ rule, so they depend on their operating frequency (generally from 2 MHz to 12 MHz for standard imaging probes) and speed of sound in each material. Matching layer are generally manufactured from epoxy resin loaded with metallic particles. In the configuration with grounded conductive layer 401 (see FIGS. 1 and 2) the first matching layer 601 is generally placed above such grounded layer 401. In case of wiring connection 401' as in FIG. 3, the first matching layer 601 is in direct contact with the piezoelectric elements 301.

Typically, the first matching layer 601 is made of a material having an acoustic impedance of about 5 to 12 MRayl and the last matching layer 701 has an acoustic impedance of about 2 MRayl.

As a last element, on the matching layer 701, an acoustic lens 801, typically of silicone rubber, is placed which forms the interface between the head of the probe 1 and the surface of a target body. The aim of such a lens is to focus the ultrasound beam in the elevation plane.

The contact terminations 201 and 501 of the layer 101 formed by the array of contact electrodes and of the layer 401 or wires 401' formed by the grounded conductive material are electrically and mechanically connected to a printed circuit board 4 which provides the necessary conductive tracks which are connected to a probe connection cable (not shown) via connector 8 and which cable connects the probe with an ultrasound apparatus as for example an ultrasound imaging apparatus.

A multi-element ultrasonic transducer array is generally formed from a block of piezoelectric material, which may be either a ceramic or a polymer. The block is cut or diced into one or more rows of individual elements to form the array. The element-to-element spacing is known as the "pitch" of the array and the spaces between individual elements are known as "kerfs." The kerfs may be filled with some filler material, generally a damping material having low acoustic impedance that blocks and absorbs the transmission of vibrations between adjoining elements, or they may be air-filled. The array of elements may be left in a linear configuration in which all of the elements are in a single plane, or the array may be bent or curved for use as a convex or concave array.

Before the piezoelectric material is diced into individual array elements it is generally coated with metallic electrode material on the top (also referred to as the front or transmit/receive side) and bottom of the bar. The electrodes on the top of the elements are conventionally connected to an electrical reference potential or ground, and individual conductors are attached to electrode areas on the bottom of the bar to electrically connect to each subsequently formed element. These conductors are then conventionally potted in an acoustic backing material as described, for example, in U.S. Pat. No. 4,825,115 which fills the space below the transducer elements and between the wires, and damps acoustic vibrations emanating from the bottom of the transducer array. Alternately, the conductors and backing material may be preformed in a block of backing material containing parallel spaced wires, which is then attached to the piezoelectric as described in U.S. Pat. Nos. 5,329,498 and 5,267,221. The piezoelectric bar and electrodes are then diced while attached to the backing material. As the bar is diced into individual elements, the metal plating is simultaneously cut into individual electrically separate electrodes for each transducer element. The transducer is completed by bonding front matching layers and the acoustic lens.

Figure 4:
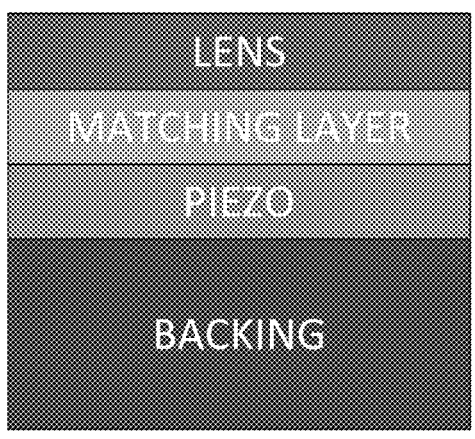
FIG. 4 schematically shows the cross section of a conventional ultrasound transducer.

The result is a stack of layers starting from the backing 2 to the acoustic lens 801 as exemplary shown in FIG. 4.

The backing material 2 acts both as a support and as a damping device for the back-travelling acoustic wave, to minimize reverberations and ringing. Backing material is generally a special hard rubber compound with poor thermal conductivity. A metallic, typically aluminium, block 3 acts as a support for the backing material 2. Where the term "backing" occurs it is understood as meaning a solid mass, of suitable geometry, on which the piezoelectric elements are mounted; when this component is excited by a voltage pulse, the oscillation is dampened and the reduction in the amplitude between successive oscillations depends on the material with which the component is combined. This base must therefore have particular acoustic properties in terms of impedance and absorption in order to obtain the desired level of attenuation.

This mechanism, nevertheless, causes the loss of a substantial part of the energy generated by the piezoelectric active material, because half of it is directed downward, towards the backing, and is lost into it being converted into heat.

Figure 5:
FIG. 5 schematically shows the cross section of an ultrasound transducer including an acoustic mirror.

Thus the idea of using a reflecting interface (also called acoustic mirror or back-matching or de-matching layer in the present disclosure) between backing and piezo material as exemplary shown in FIG. 5 to allow more energy to be directed towards the front face resulting in a stronger pulse, thus enhanced sensitivity and reduced heating.

Figure 7:
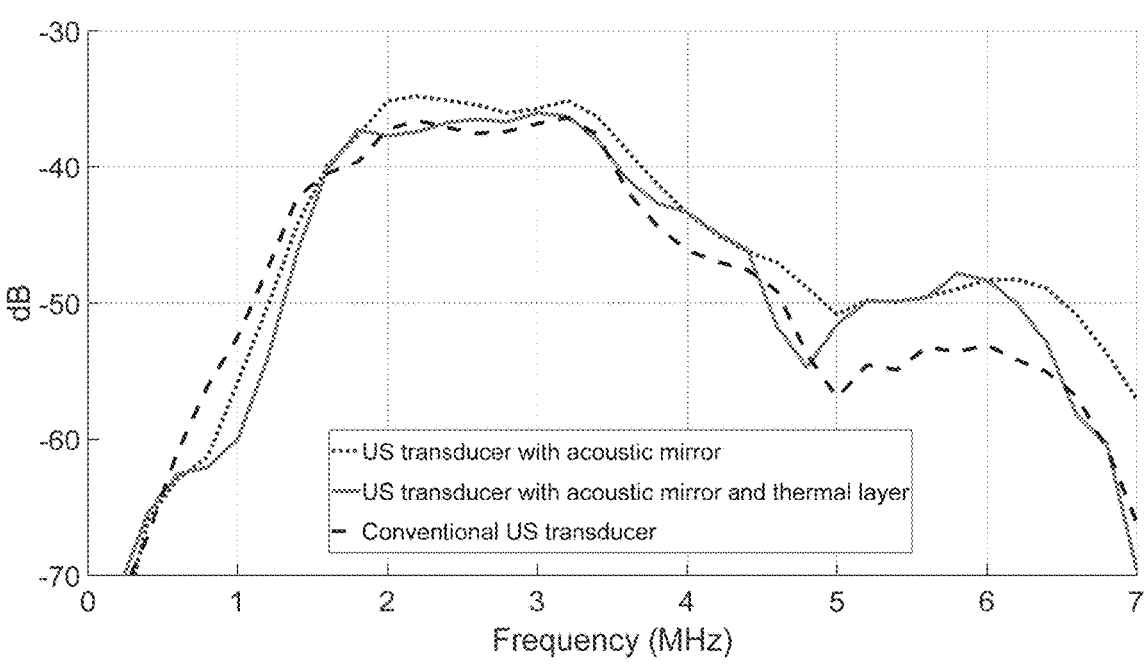
FIGS. 7 and 8 respectively show the bandwidth and the pulse envelope of a traditional transducer, a transducer with low-impedance acoustic mirror and a transducer with acoustic mirror and thermal layer according to embodiments herein. The time length of the pulse at −20 dB are 1.18 μs, 1.15 μs and 1.23 μs respectively.
Figure 8:
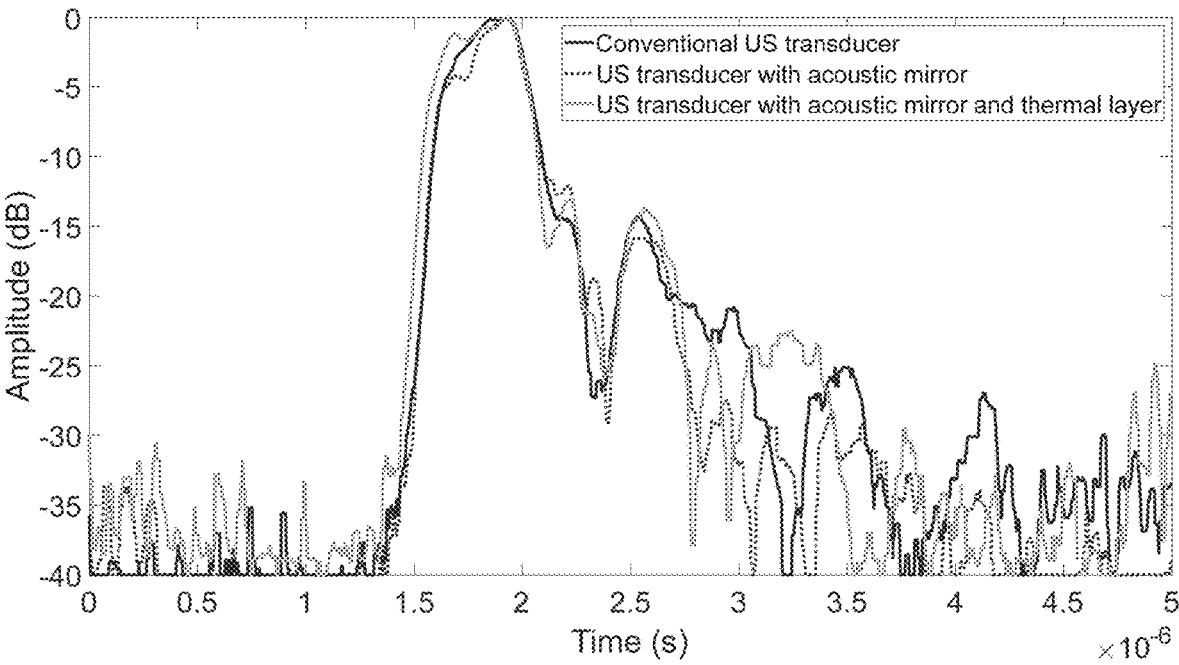
Figure 9:
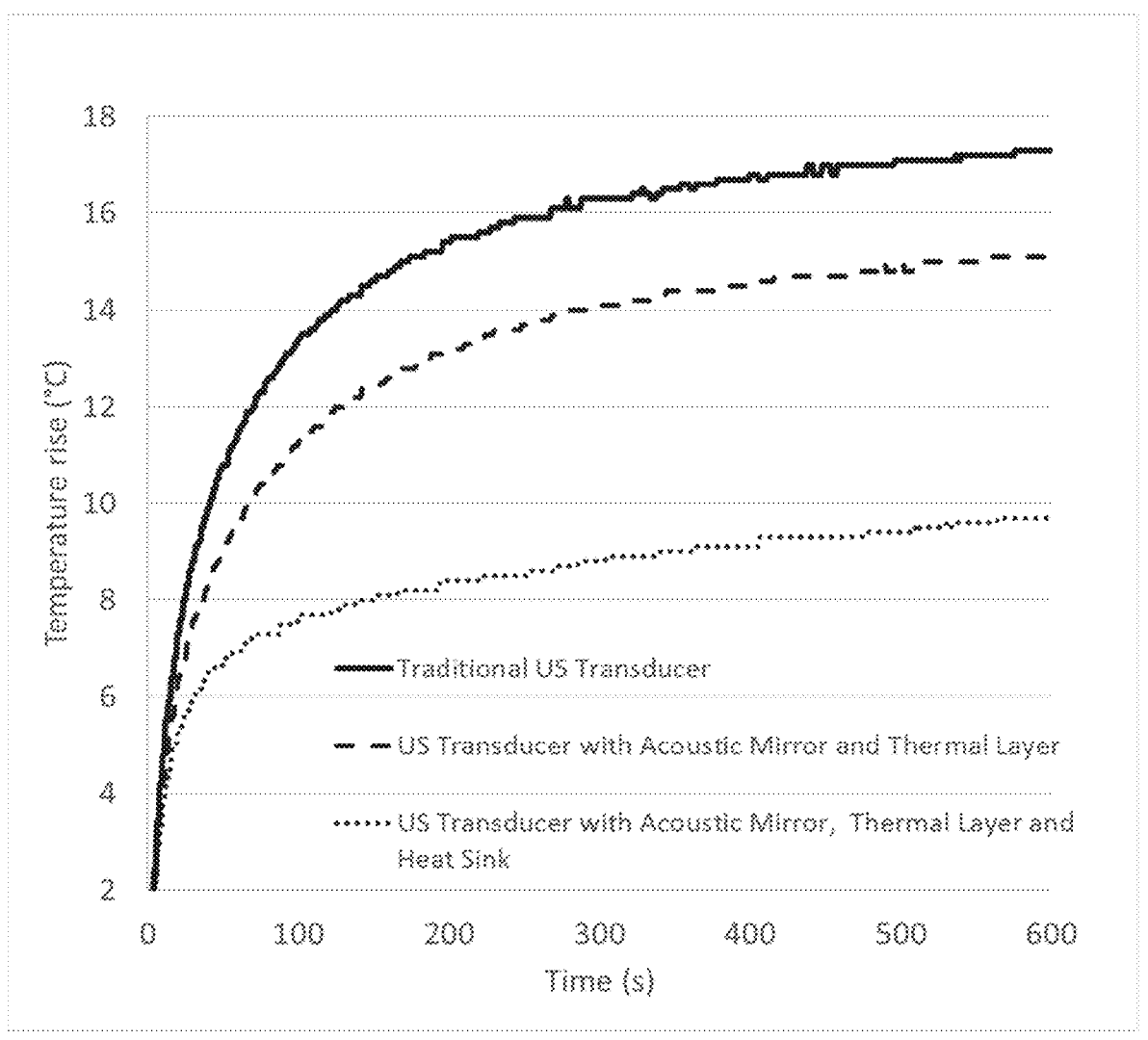
FIG. 9 shows the lens temperature rise of a traditional transducer, a transducer with low-impedance acoustic mirror and thermal layer and a transducer with acoustic mirror, thermal layer and heat sink according to embodiments herein.

As it is not always possible to use a reflecting interface that is also thermally conductive, embodiments herein propose an arrangement for improving heat efficiency therefore to limit the lens temperature in transducer assemblies having a back-matching layer as, for example, disclosed in US 2018/0290175 to be herein incorporated by reference. A layer (herein referenced as thermal layer or heat transfer layer) with high acoustic impedance and high thermal conductivity is placed between the back-matching layer and the backing as exemplary shown in FIG. 6. The additional thermal layer in the rear part of the acoustic stack does not significantly affect the acoustic performances (bandwidth and pulse length) of the transducer, but increase thermal efficiency as it can be appreciated by looking at FIGS. 7 to 9 for a specific example with materials having an acoustic impedance Z falling in the following ranges:

| Component/element | Z (MRay1) |
| --- | --- |
| Piezo-material | 20-30 |
| Matching layer(s) | 2-14 |
| Acoustic mirror | 2-5 |
| Thermal layer | 80-100 |
| Backing | 3-10 |
| Lens | 1-1.5 |

The thermal layer not only allows to create a thermal circuit that drain heat, but also to reduce the energy that needs to be dissipated due to the following considerations.

The amounts of acoustic energy reflected and transmitted at the interface between two media 1 and 2 depend on the value of the acoustic impedance $Z_1$, $Z_2$ of such media. The amplitudes of the incident (Pi), reflected (Pr) and transmitted (Pt) pressure waves are related by the transmission and reflection coefficients, T and R respectively, by the following formula $$R = \frac{Z_2 - Z_1}{Z_2 + Z_1}, T = \frac{2Z_2}{Z_2 + Z_1}.$$

Figure 10:
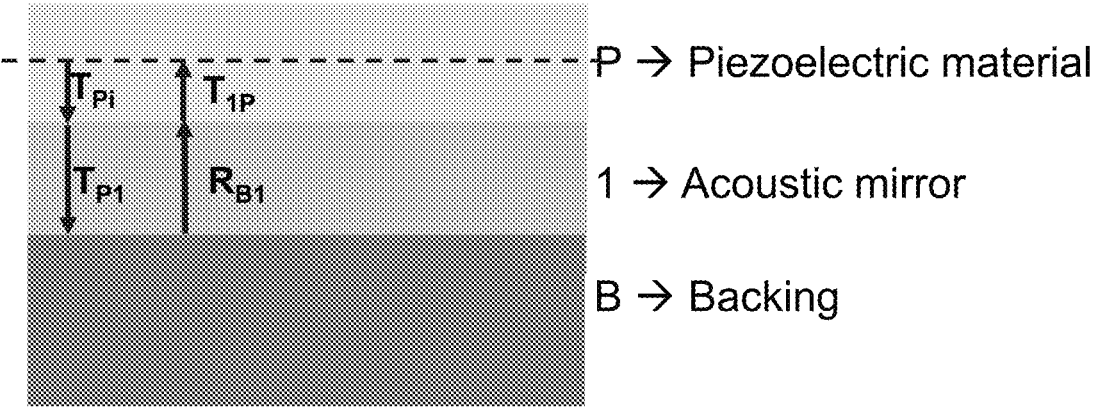
FIGS. 10 and 11 respectively schematically show the acoustic energy transmitted and reflected in the rear part of a transducer with low-impedance acoustic mirror and a transducer with acoustic mirror and thermal layer according to embodiments herein.
Figure 11:
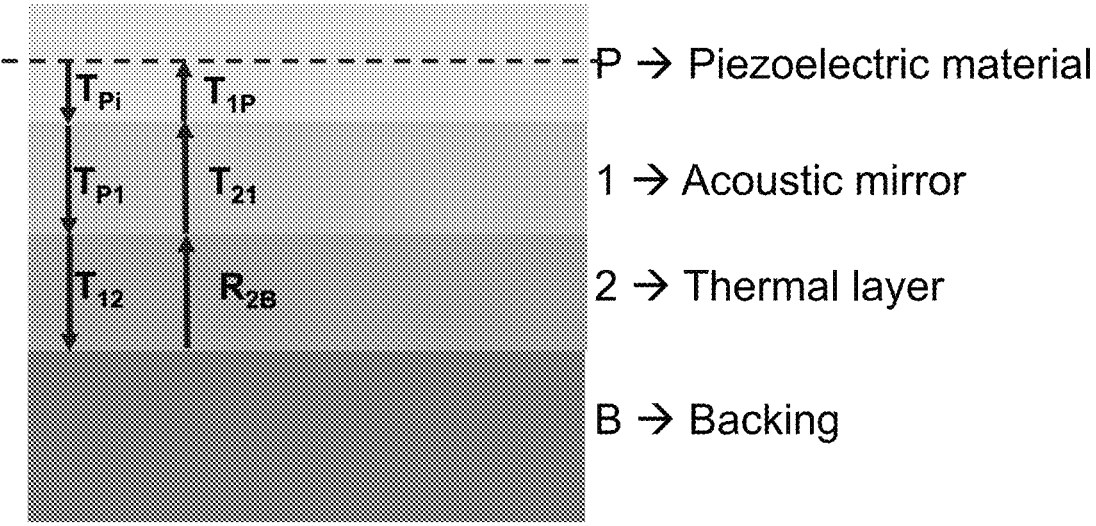

As an example, in the case shown in FIG. 10, the percentage of acoustic energy reflected at the interface acoustic mirror/backing layer is $$R_{1B,TOT} = T_{P1} \times R_{1B} \times T_{P1} \sim 0.13\%,$$

where $T_{P1}$ is the transmission coefficient at the interface piezo-material (P)/acoustic mirror (1), $R_{B1}$ is the reflection coefficient at the interface backing (B)/acoustic mirror (1) and $T_{1P}$ is the transmission coefficient at the interface acoustic mirror (1)/piezo-material (P). This formula considers that the total amount of energy reflected at the interface backing/acoustic mirror and detected by the piezo-material ($R_{1B,TOT}$) is due to the superposition of the transmitted and reflected contributes at each interface along the path. Using this principle of superposition, we can show that in the case shown in FIG. 11, where a thermal layer is added between the backing and the acoustic mirror, the reflected energy is increased as the percentage of the total acoustic energy ($R_{2B,TOT}$) reflected at the interface thermal layer (2)/backing layer (B) can be calculated as follows $$R_{2B,TOT} = T_{P1} \times T_{12} \times R_{2B} \times T_{21} \times T_{1P} \sim 2\%.$$

where $T_{12}$ is the transmission coefficient at the interface acoustic mirror (1)/thermal layer (2), $R_{2B}$ is the reflection coefficient at the interface thermal layer (2)/backing (B), $T_{21}$ is the transmission coefficient at the interface thermal layer (2)/backing (B).

To maximize the heat dissipation away from the lens (therefore from the patient), the thermal layer may be connected to a heat-conducting-base support, typical made of metal, that helps to drain the heat, also called in the present disclosure heat sink.

Figure 12:
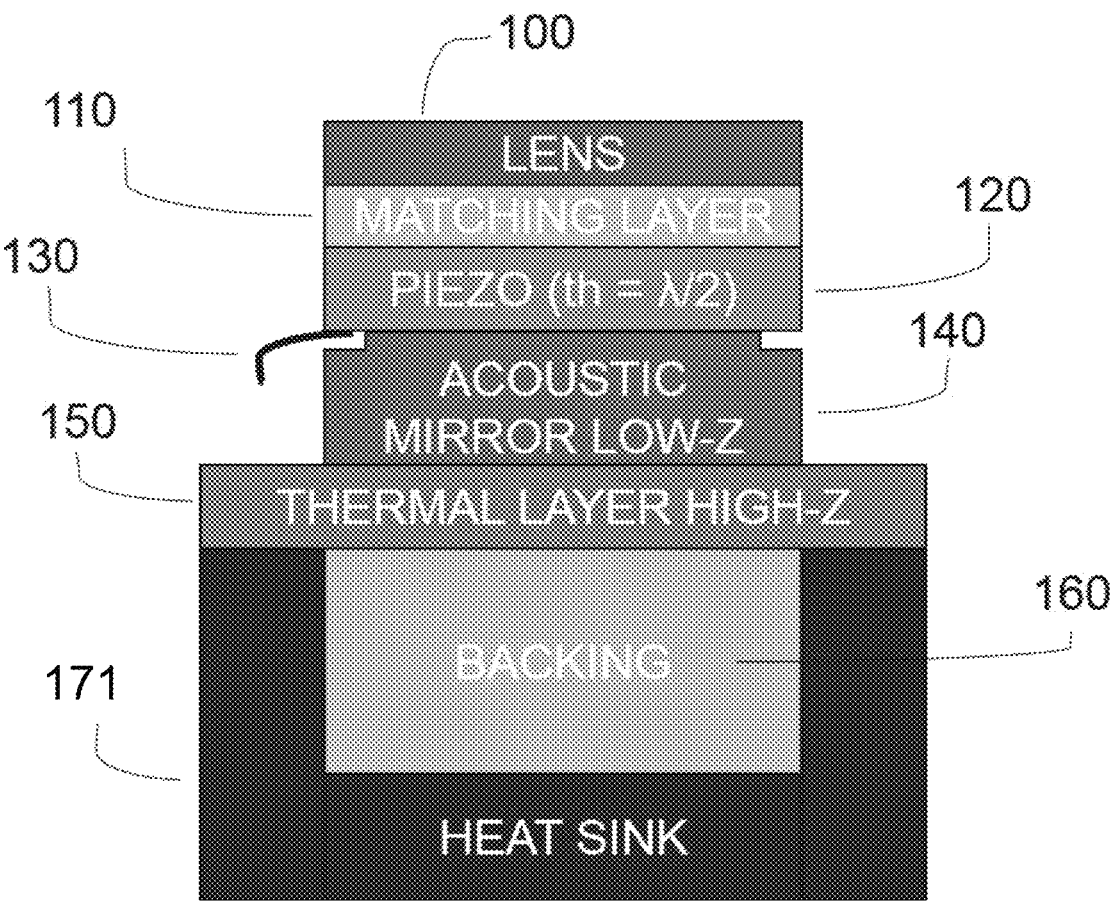
FIG. 12 schematically shows the cross section of an ultrasound transducer according to an embodiment where the thermal layer is in thermal contact with a heat sink enclosing the backing of the transducer.
Figure 13:
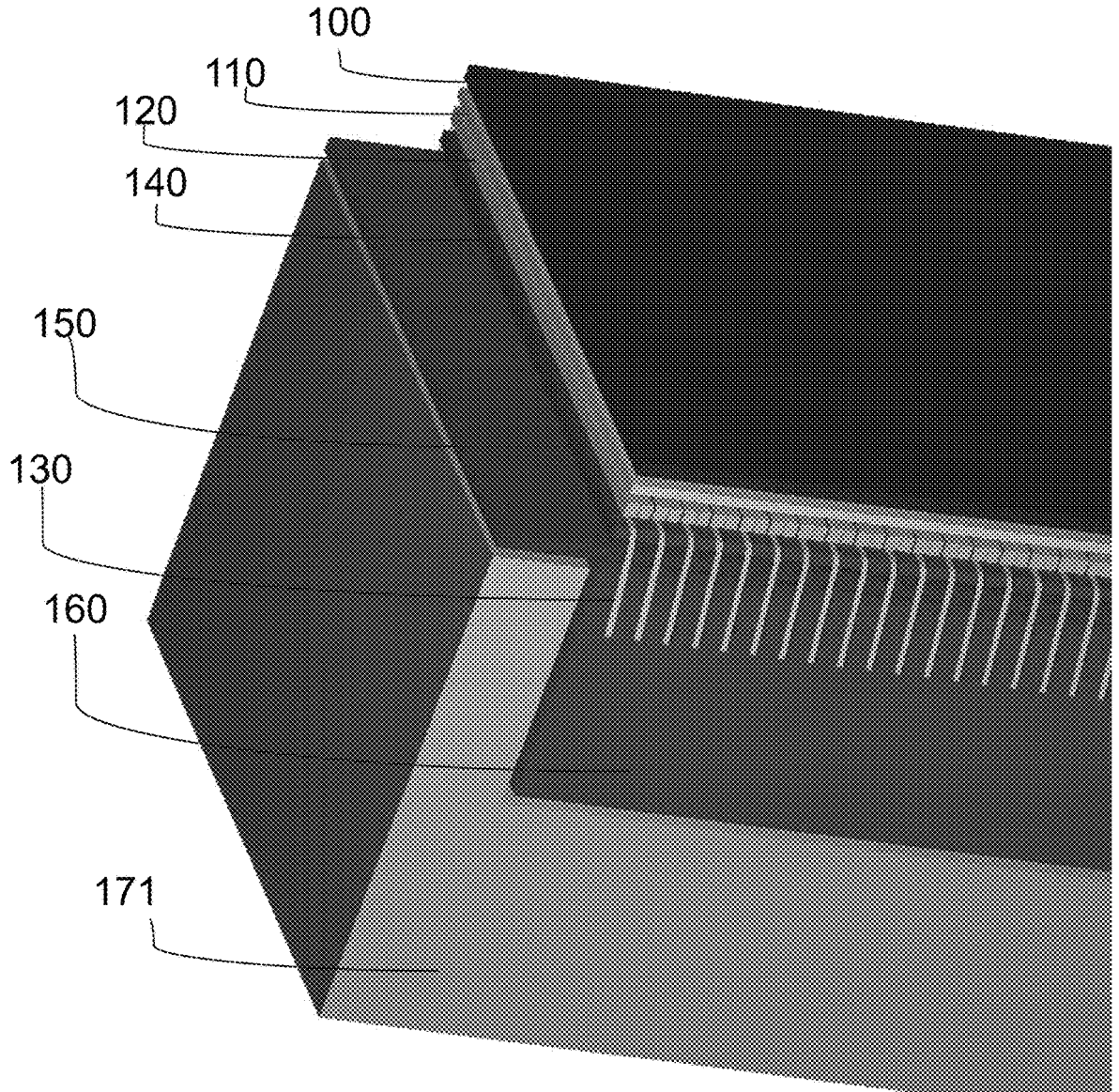
FIG. 13 is a perspective view of the transducer of FIG. 12.

The cross section of an exemplary acoustic stack with high thermal heat sink system according to an embodiment herein is shown in FIGS. 12 and 13. The heat sink 171 is distinguished by a "U" shape/bracket shape to contact the thermal layer high-Z 150. Particularly the thermal circuit comprises a U-shaped portion surrounding the backing layer to form, together with the heat transfer layer, a closed loop circuit around the backing layer. The interface between heat sink 171 and thermal layer high-Z 150 may be filled with thermally conductive paste, in order to dissipate the temperature of thermal layer high-Z 150 towards the heat sink 171.

Figure 14:
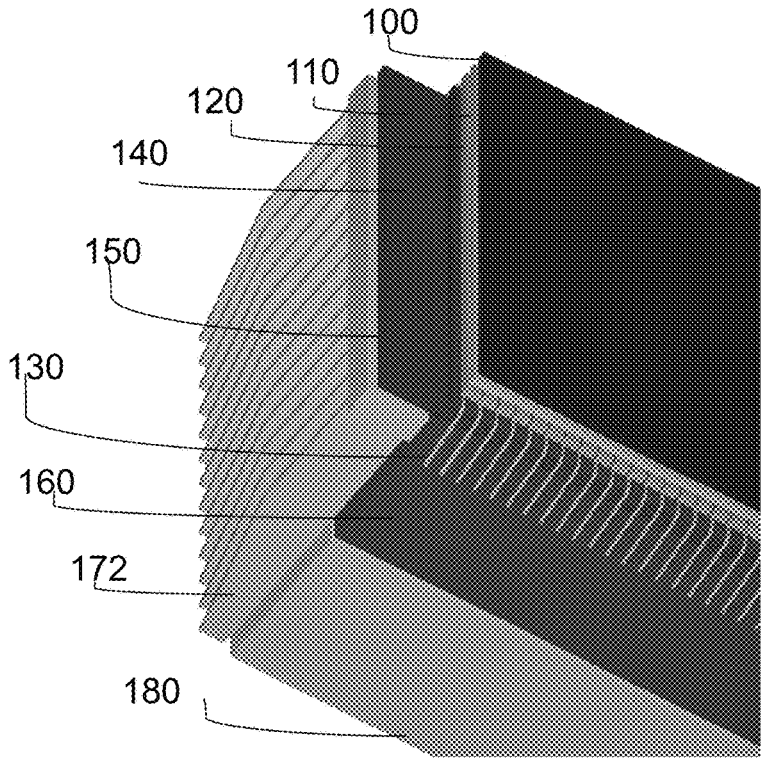
FIGS. 14 and 15 show, respectively, a perspective and a cross section view of an ultrasound transducer according to another embodiment where the thermal layer is in contact with a heat sink through a lamellar element.
Figure 15:
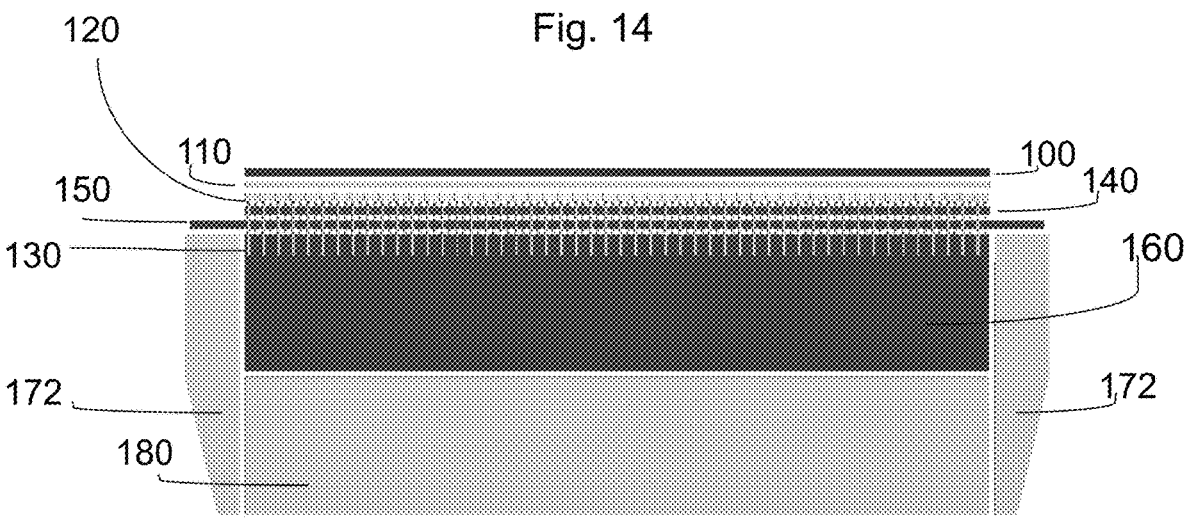

In the embodiment shown in FIGS. 14 and 15, the heat sink 172 is characterized by fins or a lamellar shape to increase heat dissipation. The heat sink 172 is mounted on the two sides (left and right) of the acoustic stack. The interface between heat sink 172 and thermal layer high-Z 150 may be advantageously filled by thermally conductive paste, in order to improve the transport of heat from the thermal layer high-Z 150 towards the heat sink 172. The heat sink may be made by metal material (e.g. aluminum, copper) or by graphite layers or graphene or doped epoxy resins, in which the thickness of each lamellar is preferably in the range [0.1÷1.0] mm. Fins are typically in the range [0.1÷0.2] while aluminum extruded dissipaters are typically in the range [0.9÷1.0]. This range has been chosen in order to make greater the exchange surface between the heat generated by the acoustic stack and the ambient. The heat sink 172 may be connected to a support 180, that acts both as a support for the mechanical structure of the acoustic stack and as residual heat collector.

Figure 16:
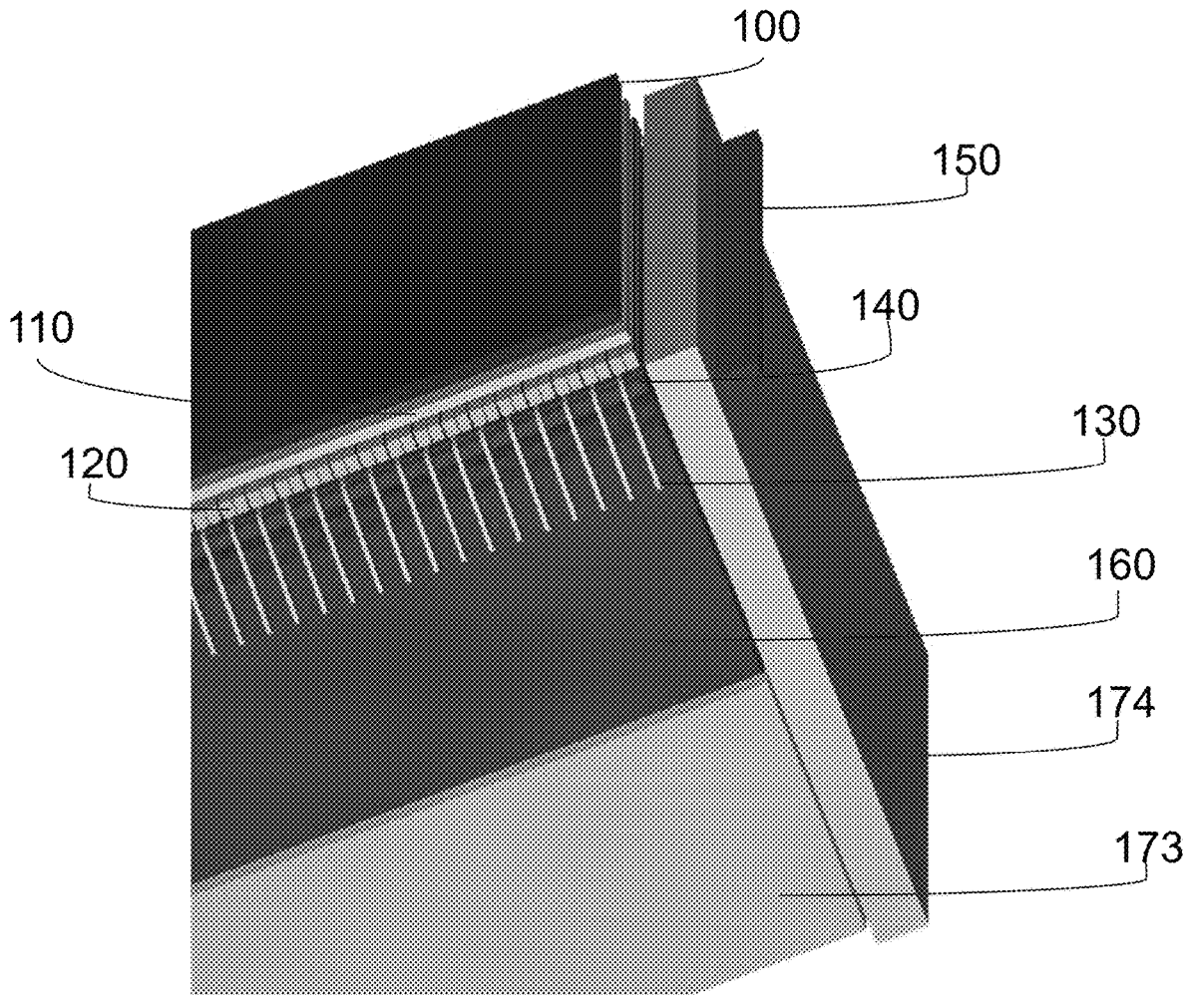
FIG. 16 is a perspective view of an ultrasound transducer according to a further embodiment where a split for connecting the thermal layer with the heat sink is shown.

In a further embodiment as shown in FIG. 16, the thermally conductive layer 150 has a rectangular or square shape with a split extension for connection with the metal support 173 through a thermally conductive element 174, for example made by metal, graphite or graphene, typically mounted on the two sides (left and right) of the acoustic stack. The indicated shape is only an example. Other shapes are possible as long as they allow a mechanical coupling between the thermally conductive layer 150 and the thermally conductive element 174. Also the support 173 may be mechanically coupled with the element 174 using splits and protrusions or other similar coupling elements. Bonding can be equivalently used, for example with a thermally conductive resin.

In an embodiment, the split of thermal layer 150 is inserted in an opening of the thermally conductive element 174 or vice versa. The free space can be filled by thermally conductive paste in order to improve the dissipation of thermal layer high-Z 150 towards support 173. The latter can be made preferably by metal material (e.g. aluminum), graphite or graphene.

The heat sinks 171, 172, the support 173, 180, the thermally conductive layer/element 150, 174 of any configuration may be thermally connected to the probe case by a thermally conductive filler, so that the ability of the probe to spread heat to the environment is governed primarily by passive free convection of heat from the external surfaces of the probes. Of course there is a limit in the capacity to remove heat by natural convection of air from the external probe surface, that depends by the efficiency of the designed thermal path and the span of dissipation effective surface area. An improvement may consist in spreading some of the heat down the length of the attached cable in order to extend the passive convection surface area. A further improvement may contemplate the usage of a dissipater mechanically connected with the support 173, typically in aluminium, to increase the surface for thermal exchange or other similar solutions.

A particularly advantageous option is to consider an internal filling material that may act as a heat storage device, subtracting heat at a fixed temperature by means of a phase transition process. Such material can be a Phase Changing Material (PCM) compound that can be dispersed, for example, in any void space available in the probe, particularly in the rear part of it.

The usage of a PCM in an ultrasound probe is known, for example, from U.S. Pat. No. 7,308,828 and EP Pat. No. 2,992,829. Example of PCMs can be found in Kenisarin, M. Mahkamov, K (2007), "Solar energy storage using phase change materials", Renewable and Sustainable Energy Reviews 11 (9): 1913-1965 and Sharma, Atul; Tyagi, V. V.; Chen, C. R.; Buddhi, D. (2009), "Review on thermal energy storage with phase change materials and applications", Renewable and Sustainable Energy Reviews 13 (2): 318-345 to be considered herein incorporated by reference.

Figure 17:
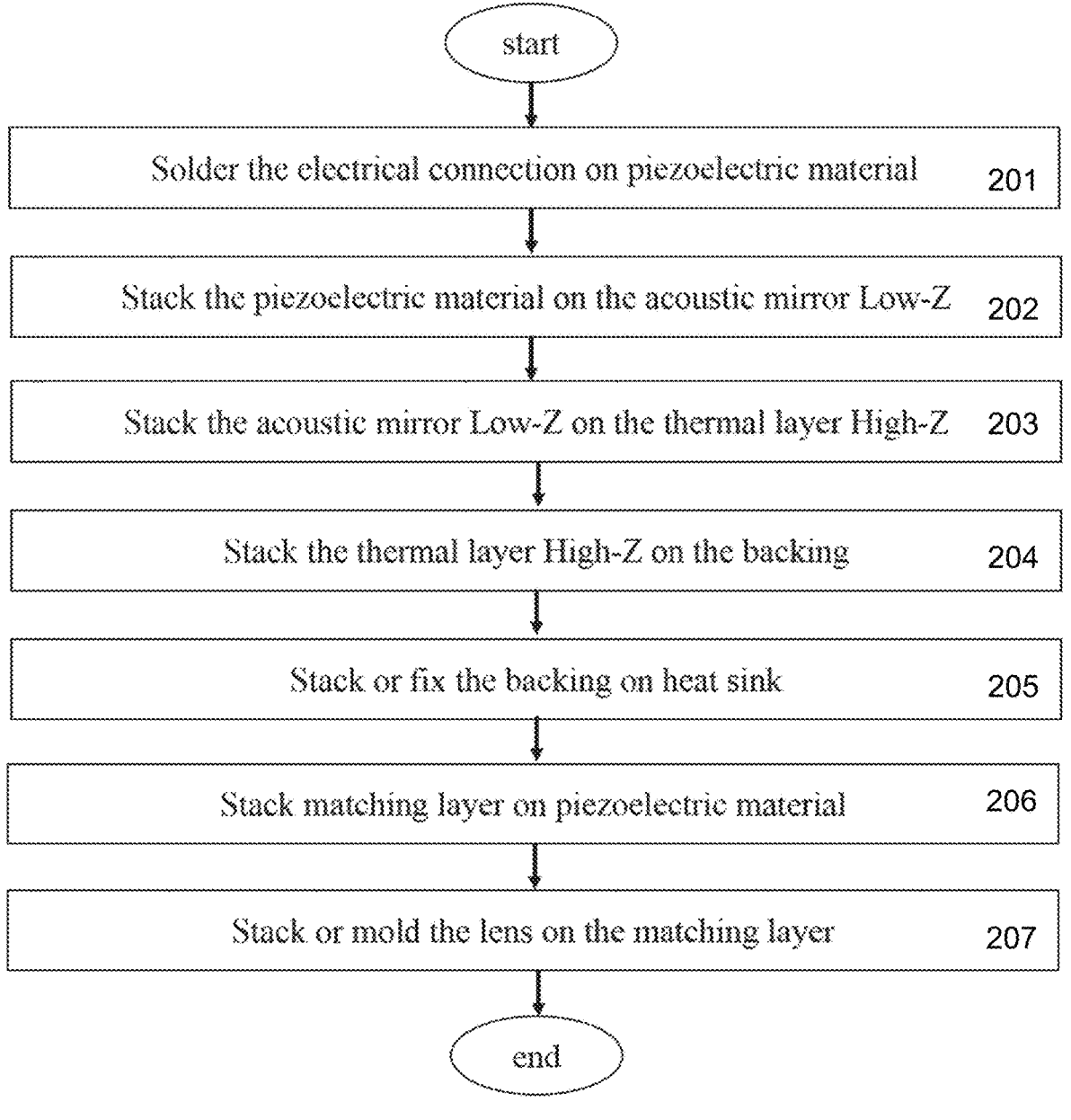

FIG. 17 shows a flowchart of an exemplary process for manufacturing an acoustic stack according to embodiments herein.

At 201, the electrical connection 130 is soldered on piezoelectric material 120. At 202, the latter is stacked on the acoustic mirror Low-Z 140 by means of bonding. The bonding operation may be carried out using non-conductive adhesive. The acoustic mirror low-Z 140 may be formed by mold directly on the piezoelectric material 120. At 203, the acoustic mirror low-Z 140 is stacked on the thermal layer high-Z 150. The acoustic mirror low-Z 140 may be formed by mold directly on the thermal layer high-Z 150.

At 204, the thermal layer 150 is stacked on backing 160. At 205, the latter is bonded or mechanically fixed on high thermal heat sink system 171, which functionality is two-fold: the first, mechanical support for the acoustic stack; the second, heat sink for limiting the temperature on the top of acoustic stack (i.e. lens 100). The heatsink system 170 is in direct contact with the thermal layer high-Z 150. The contact can be improved by filling the gap using thermally conductive paste, in order to dissipate better the temperature of thermal layer high-Z 150 towards general heat sink 170. At 206, matching layer or layers 110 are stacked on piezoelectric material 120 by means of bonding. The bonding operation may be carried out using non-conductive adhesive. The matching layer(s) 110 could also casted directly on the piezoelectric material. At 207, lens 100 is formed by means of mold (injection of material with low acoustic impedance like the human skin, e.g. silicone) or by bonding a pre-fabricated lens with non-conductive adhesive.

It should be noted that the method of manufacturing of the proposed acoustic stack apparatus is not limited to the sequence described above, and the processes of the method may be performed in a different sequence.

Figure 18:
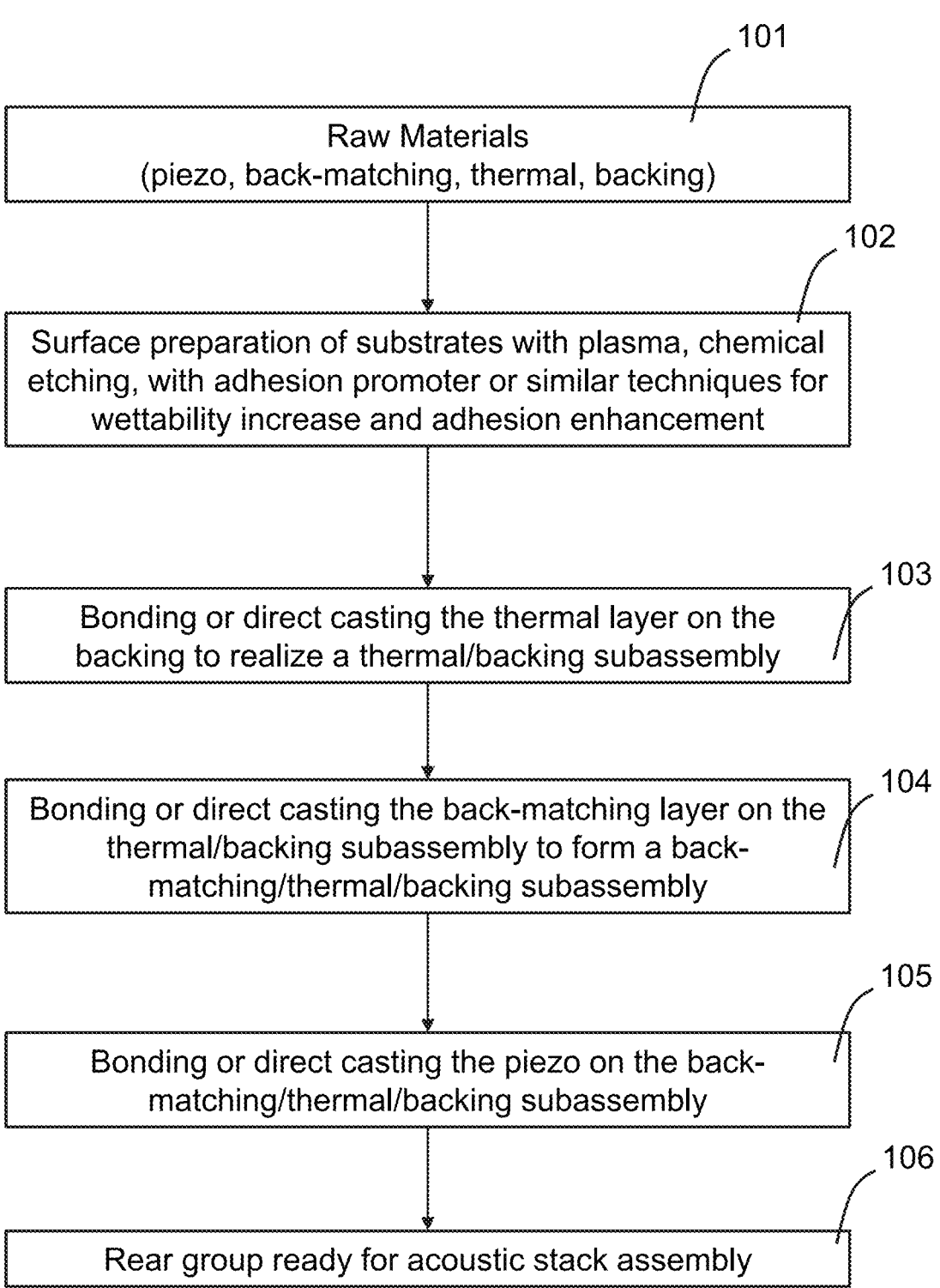

Several options are available for forming the stack. With reference to FIG. 18, a process starting from the backing is illustrated.

At 101 Raw Materials (piezo 120, back-matching 140, backing 160, heat transfer layer 150) are provided.

At 102 the surfaces are prepared for bonding/casting.

At 103 the heat transfer layer 150 is casted or bonded on the backing 160 to realize a thermal/backing subassembly.

At 104 the back-matching layer 140 is casted or bonded on the thermal/backing subassembly to form a matching/thermal/backing subassembly.

At 105 the piezo material is casted or bonded on the matching/thermal/backing subassembly.

The process is completed by bonding/casting the matching layer(s) 110 and adding the lens 100.

Figure 19:
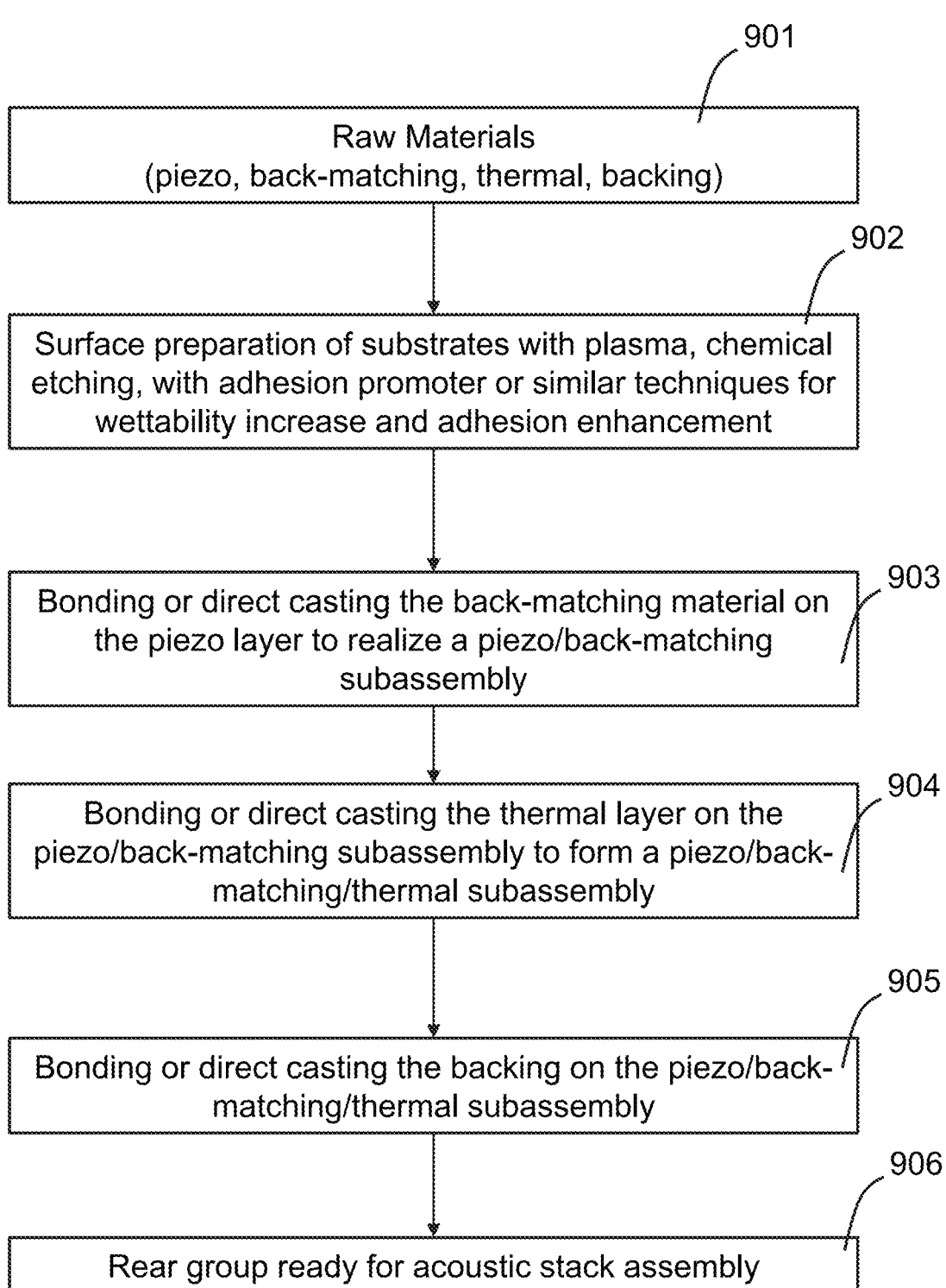

With reference to FIG. 19, an alternative process starting from the piezo layer is illustrated.

At 902 the surfaces are prepared for bonding/casting.

At 903 the back-matching layer 140 is casted or bonded on the piezo layer 120 to form a piezo/matching subassembly.

At 904 the thermal layer 150 is casted or bonded on the piezo/matching subassembly to form piezo/matching/thermal subassembly.

At 905 the backing 160 is casted or bonded on the piezo/matching/thermal subassembly.

Alternatively, the thermal layer 150 may be casted or bonded on the backing 160 and the subassembly so obtained bonded to the piezo/matching subassembly.

Figure 6:
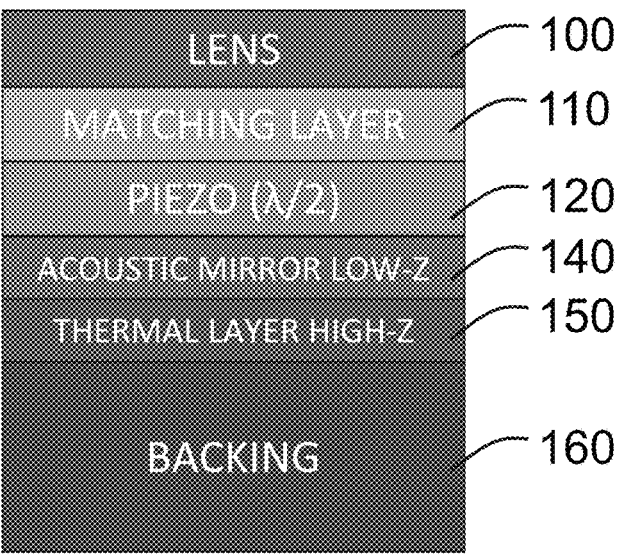
FIG. 6 schematically shows the cross section of an ultrasound transducer according to an embodiment herein.

Any possible combination of bonding/casting of layers is to be considered included in the present disclosure to arrive at the stack shown in FIG. 6 including piezo material 120, de-matching layer 140, thermal layer 150, backing 160. For example, layers may be bonded/casted in pairs and the resultant subassemblies bonded together.

The stack so obtained is already capable of draining heat thanks to the thermal layer 150. To improve thermal efficiency, the thermal layer is put in thermal contact with other elements working as heat sinks or thermal dissipators or thermal storage devices.

To such extent, a process according to embodiments herein further comprises providing an element of thermal conductive material to be put in thermal contact with the thermal layer. Such element may have a U-shaped to form a receptacle for the backing with lateral walls free to contact radial extensions of the thermal layer. The process, as illustrated in FIG. 20, thus may comprise bonding or mechanically coupling (for example through fixing elements like screws) such U-shaped element on the backing to obtain the device as shown in FIGS. 12 and 13. Contact between the lateral walls and the thermal layer may be improved using thermal conductive paste. In an alternative configuration not shown in the figures, the U-shaped element has vertical protrusions to be inserted in corresponding openings obtained in the thermal layer for example through grinding operations.

Figure 21:
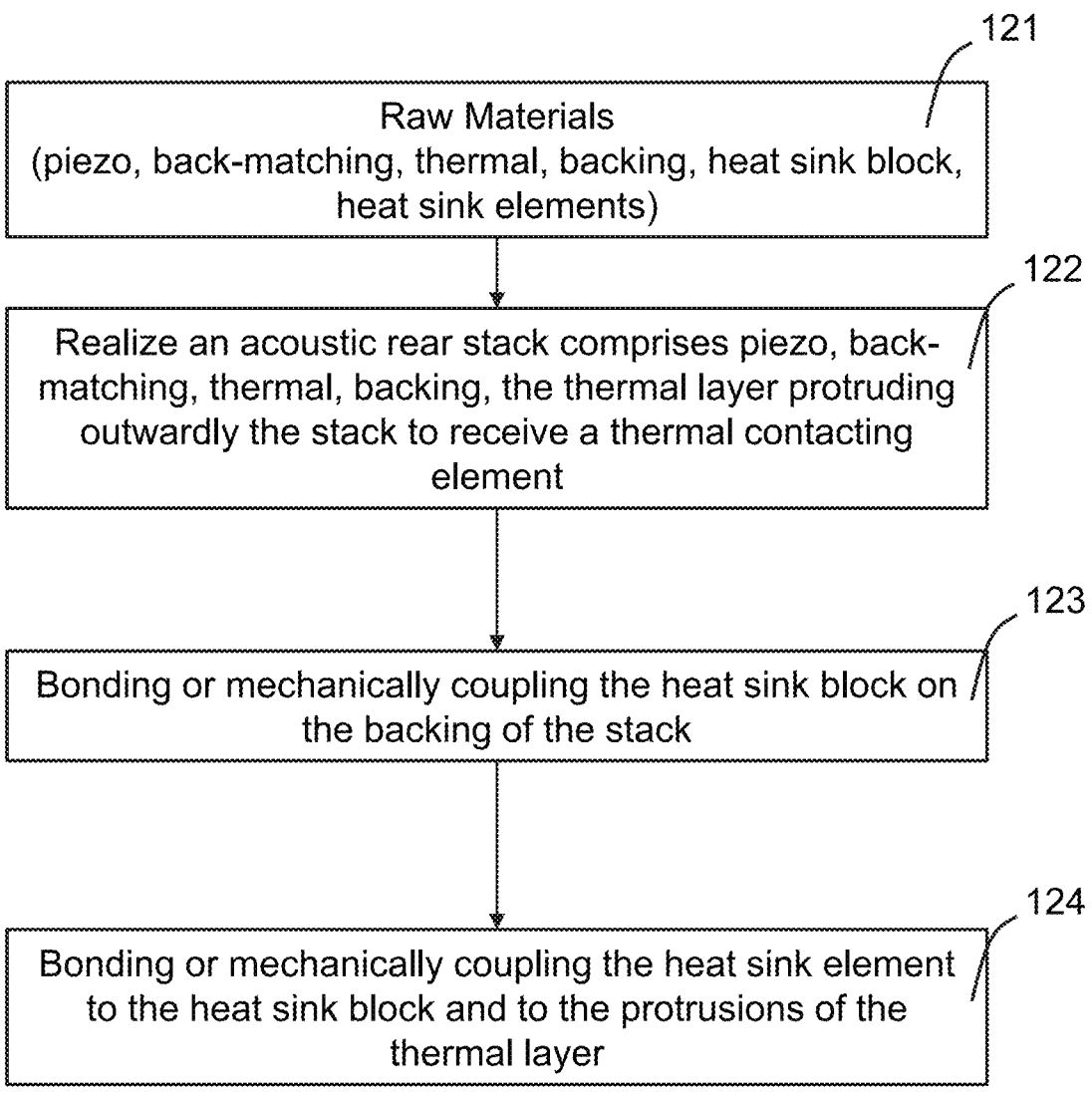

The thermally conductive material may also be in the form of a block to be put in contact with the thermal layer through further elements like pillars or vertical walls. In an advantageous configuration such further element have a lamellar shape and/or include fins to form a thermal dissipators as shown in FIGS. 14 and 15. The process according to a further embodiment thus correspondingly comprises, as illustrated in FIG. 21, providing a block of thermal conductive material like a metal such as aluminium, providing lateral thermal conductive elements, bonding or mechanically coupling the block to the backing and the lateral conductive elements to the block and the thermal layer.

In an advantageous configuration, the lateral conductive elements are in the form of a wall having at least one aperture for receiving a protruding part of the thermal layer to obtain an interlocking coupling as shown in FIG. 16. Also the block may have a protrusion for coupling with another opening of the lateral conductive elements.

A corresponding manufacturing process thus comprises providing lateral conductive elements, having apertures and thus mechanically coupling such apertures with corresponding protrusions of the thermal layer and/or of the thermally conductive block.

All the process steps can be performed in any meaningful order and are not all necessary. For example grinding and dicing steps are obviously optional in all the embodiments herein disclosed as well as the surface preparation that can certainly be omitted. A variant could be to use adhesive properties of the back-matching layer to allow a direct bonding to piezo. All without departing from the guiding principle of the invention disclosed above and claimed below.

The invention claimed is:

1. A transducer assembly operable to transmit ultrasonic energy in a desired direction towards a zone adapted to be acoustically coupled to an object or area of interest, the transducer assembly comprising:
   a) a transducer layer;
   b) a backing layer disposed behind said transducer layer with respect to the desired direction;
   c) a back-matching layer disposed between the transducer layer and the backing layer to reflect towards said transducer layer part of the ultrasonic energy directed from the transducer layer to the backing layer;
   d) a heat transfer layer disposed between the back-matching layer and the backing layer to drain heat from the transducer assembly;
   e) wherein the heat transfer layer is bonded or casted on the back-matching layer, or the back-matching layer is bonded or casted on the heat transfer layer.

2. Transducer assembly according to claim 1, wherein the heat transfer layer is in contact with the back-matching layer either directly or through a bonding layer.

3. Transducer assembly according to claim 1, wherein the heat transfer layer is in thermal communication with a heat dissipating and/or storing device.

4. Transducer assembly according to claim 1, comprising a heat-conductive element at one side of the assembly contacting the heat transfer layer to drain heat from the transducer assembly.

5. Transducer assembly according to claim 4, wherein the heat-conducting element comprises a heat-conductive structure chosen from a lamellar structure or structure comprising fins to dissipate at least partially the drained heat.

6. Transducer assembly according to claim 4, wherein the heat conducting element is in thermal contact with a dissipating or accumulating element.

7. Transducer assembly according to claim 4, wherein at least one heat-conductive element has a slot for receiving a portion of the heat transfer layer or a lateral protrusion thereof.

8. Transducer assembly according to claim 1, further comprising two heat-conductive elements at opposite sides of the assembly in thermal contact with the heat transfer layer to drain heat from the assembly.

9. Transducer assembly according to claim 8, wherein the heat-conductive element or elements are in thermal contact with a dissipating or accumulating element located in the rear part of the assembly opposite to the zone adapted to be acoustically coupled to the object or area of interest.

10. Transducer assembly according to claim 1, wherein the heat transfer layer extends laterally from the transducer assembly to expose at least one surface for thermal contact, direct and/or indirect through conductive materials, with an element of a thermal circuit.

11. Transducer assembly according to claim 10, wherein the thermal circuit comprises a U-shaped portion surrounding the backing layer to form, together with the heat transfer layer, a closed loop circuit around the backing layer.

12. Transducer assembly according to claim 11, wherein the U-shaped portion is a single-piece element having a bracket shape.

13. Transducer assembly according to claim 1, wherein the back-matching layer has an acoustic impedance less than 10 MRayl.

14. Transducer assembly according to claim 1, wherein the back-matching layer has an acoustic impedance between 2 and 5 MRayl.

* * * * *